United States Patent
Winter et al.

(10) Patent No.: US 8,718,352 B2
(45) Date of Patent: May 6, 2014

(54) SYSTEM AND METHOD FOR TESTING ROPES

(75) Inventors: Sven Winter, Burgstall (DE); Dirk Moll, Dettingen unter Teck (DE); Ralf Eisinger, Ulm (DE); Konstantin Kuehner, Stuttgart (DE); Egon Guttengeber, Obergriesbach (DE); Andreas Proehl, Munich (DE); Markus Eichinger, Turkfield (DE)

(73) Assignee: Winspect GmbH (DE)

( * ) Notice: Subject to any disclaimer, the term of this patent is extended or adjusted under 35 U.S.C. 154(b) by 290 days.

(21) Appl. No.: 13/095,364

(22) Filed: Apr. 27, 2011

(65) Prior Publication Data

US 2011/0268313 A1  Nov. 3, 2011

(30) Foreign Application Priority Data

Apr. 28, 2010 (EP) .................................. 10004488

(51) Int. Cl.
 *G06K 9/00* (2006.01)
(52) U.S. Cl.
 USPC ........... 382/141; 382/108; 382/152; 382/257; 382/286; 382/308; 382/111; 187/251; 187/414; 187/411
(58) Field of Classification Search
 CPC ................... G06T 7/0004; G06T 2207/30108; G01N 21/952; G01N 21/8806; G01N 2021/8854; G01N 2021/8927; G01N 21/896
 USPC ......... 382/141, 108, 152, 257, 286, 308, 111; 187/251, 414, 411
 See application file for complete search history.

(56) References Cited

U.S. PATENT DOCUMENTS

| 8,254,660 | B2 * | 8/2012 | Verreet | 382/141 |
| 2003/0002830 | A1 * | 1/2003 | Petryszak | 385/111 |
| 2007/0034454 | A1 * | 2/2007 | Dold et al. | 187/411 |
| 2007/0188739 | A1 * | 8/2007 | Aoshima et al. | 356/73.1 |
| 2010/0133046 | A1 * | 6/2010 | Allwardt et al. | 187/251 |

FOREIGN PATENT DOCUMENTS

| JP | 2-56397 | 2/1990 |
| JP | 3-60312 | 3/1991 |
| WO | 2010092619 | 8/2010 |

* cited by examiner

*Primary Examiner* — Mike Rahmjoo
(74) *Attorney, Agent, or Firm* — Onello & Mello, LLP

(57) ABSTRACT

A computer-aided method, system and computer program product are provided for optical testing of a rope. Such method includes: providing an image data set for at least one portion of the rope; providing target values of a pictorial longitudinal extension of the representation of wires relative to a pictorial longitudinal extension of the rope in the image data set; determining a pictorial longitudinal extension of the wires in the image data set, including adapting an estimated longitudinal extension to the image data set; determining at least one quality value using a quality norm as a function of the determined pictorial longitudinal extension of the wires and the target values of the pictorial longitudinal extension of the wires; discriminating pictorial positions within the image data set of the rope, where at least one quality value exceeds or falls below a predetermined, assigned quality threshold value; and providing the discriminated pictorial positions.

14 Claims, 14 Drawing Sheets

```
WIREPATTERNNUMWIRES        ;  13

WIREPATTERNNUMPOINTSWIRE   ;  4
WIREPATTERNPOINTSWIRE      ; -149 60
WIREPATTERNPOINTSWIRE      ; -69 29
WIREPATTERNPOINTSWIRE      ; 50 -25
WIREPATTERNPOINTSWIRE      ; 152 -60
WIREPATTERNNUMPOINTSWIRE   ;  4
WIREPATTERNPOINTSWIRE      ; -201 63
WIREPATTERNPOINTSWIRE      ; -111 26
WIREPATTERNPOINTSWIRE      ; -16 -14
WIREPATTERNPOINTSWIRE      ; 63 -45
(...)
WIREPATTERNNUMGAPS         ;  10

WIREPATTERNNUMPOINTSGAP    ;  4
WIREPATTERNPOINTSGAP       ; -439 81
WIREPATTERNPOINTSGAP       ; -350 50
WIREPATTERNPOINTSGAP       ; -266 21
WIREPATTERNPOINTSGAP       ; -211 4
WIREPATTERNNUMPOINTSGAP    ;  4
WIREPATTERNPOINTSGAP       ; -387 81
WIREPATTERNPOINTSGAP       ; -294 46
WIREPATTERNPOINTSGAP       ; -226 22
WIREPATTERNPOINTSGAP       ; -175 4
(..)
```

```
{Beginning of wire pattern description}
Number of wire lines in the target pattern (arbitrary, typically 7-20)

Number of support points for line 1 (arbitrary, typically 2-5)
Coordinates support point 1
Coordinates support point 2
Coordinates support point 3
Coordinates support point 4
Number of support points for line 2 (arbitrary, typically 2-5)
Coordinates support point 1
Coordinates support point 2
Coordinates support point 3
Coordinates support point 4

Number of gap lines in the target pattern (typically wire line number-1)

Number of support points for line 1 (arbitrary, typically 2-5)
Coordinates support point 1
Coordinates support point 2
Coordinates support point 3
Coordinates support point 4
Number of support points for line 2 (arbitrary, typically 2-5)
Coordinates support point 1
Coordinates support point 2
Coordinates support point 3
Coordinates support point 4
```

FIG. 6

SYSTEM AND METHOD FOR TESTING ROPES

CROSS REFERENCE TO RELATED APPLICATION

The present patent application claims priority to European Patent Application No. 10 004 488.2, entitled SYSTEM AND METHOD FOR TESTING ROPES, and filed Apr. 28, 2010, the contents of which are hereby incorporated by reference in their entirety.

FIELD OF INTEREST

The present invention relates to a system and a method for testing ropes, and to a related computer program product.

BACKGROUND

Depending on the field of application, ropes are subjected to various stresses. For example when used with cableways, cranes or elevators, ropes move over rollers or are deflected by pulleys. Here, the rope with the individual wires is loaded primarily with tensile stresses and secondarily with bending and torsional stresses. Especially moving and stationary ropes have a finite service life for this reason.

In order to ensure the operational reliability of the ropes, in particular of ropes used for cableways, bridges, cranes or elevators, the ropes have to be checked on a regular basis. According to the prior art, such checks can comprise visual rope checks by a human.

Based on the known prior art, it is an object of the invention to provide a method for testing a rope, which can be performed more easily and safely and achieves an improved test result. The object is solved by the features of the independent claims. Preferred embodiments are the subject of the dependent claims.

SUMMARY

One aspect of the present invention relates to a method for the computer-aided, optical testing of a rope. The method comprises: providing an image data set for at least one portion of the rope; providing target values of a pictorial longitudinal extension $J_0$ of the representation of wires relative to a pictorial longitudinal extension L of the rope in the image data set; determining a pictorial longitudinal extension $J_m$ of the wires in the image data set, wherein determining comprises adapting an estimated longitudinal extension to the image data set; determining at least one quality value by means of a quality norm as a function of the determined pictorial longitudinal extension $J_m$ of the wires and the target values of the pictorial longitudinal extension $J_0$ of the wires; discriminating pictorial positions within the image data set of the rope, at which at least one quality value exceeds or falls below a predetermined, assigned quality threshold value; and providing the discriminated pictorial positions.

An optical rope check is possible by means of the provided image data set, wherein great physical strain for an human performing the visual check, for example by limited-space workplaces, by wrong body postures and wrong sitting positions, poor lighting conditions, and weather factors (e.g., cold, rain, wind, etc.), is advantageously avoided. A negative effect on the check result due to loss of concentration of the human performing the check can advantageously be avoided, in particular in the case of a longer test duration. Advantageously, the method according to aspects of the invention can be interrupted any time and/or be performed without supervision.

Providing the image data set can comprise optically capturing at least one portion of the rope, in particular, by means of an optical rope capturing device, so that optical capturing is advantageously possible during operation. Further advantageously, dangers posed to the testing human by, e.g., moving parts, such as rope, rope pulley, rollers, etc., are ruled out by optical capturing.

Advantageously, the provided or obtained image data set is available in electronic form and can thus be archived permanently by means of a corresponding archiving device, e.g., non-transient computer storage device. Thereby, changes of the rope condition can advantageously be detected or understood easily. In addition to the archivability of the visual rope condition, the conditions can be better understood or verified in an objective way. For a better archivability of the image data set, the obtained or provided images or raw image data can be stored with a suitable algorithm in a compressed way. The compression method can preferably be selected such that random access to an arbitrary rope position is possible, for example by a JPEG compression in sections together with a jump table in which the rope position is indexed. This compression can already be performed while the image data are obtained, so that a predetermined limited data transfer rate to the storage medium is not exceeded.

Further advantageously, the archivability of the image data set also enables monitoring the rope condition over time. Thus, it is conceivable that a temporal development of the rope condition or a defect can be noticed by assigning the same rope positions to image data recorded at different times.

Further advantageously, the test method can also be applied as a so-called "inline" check if the calculation duration of the observables to be evaluated, the computer performance, and the inline check permit this. The rope parameters, target values, and threshold values can be stipulated in a preceding configuration process.

The test method can comprise a 3D reconstruction. Since the rope geometry is usually well known, conclusions as to a deviation of the rope geometry in the three-dimensional space can be drawn from the determined deviations of the wire positions in a 2D image of the image data set. This 3D rope geometry could then be reconstructed in the three-dimensional space for a more precise visualization, and be illustrated as a model on a display device or display. The 2D image data of the image data set can be used as a texture for this 3D model in particular after a corresponding transformation.

A pictorial longitudinal extension $J_m$, $J_0$, J of the representation of wires in accordance with aspects of the invention is understood such that an image of a wire, which is included in the image data set, extends substantially along a preferred spatial direction, which can be referred to as a longitudinal extension or longitudinal direction of the wire. Wires of a rope extend spatially preferably along their longitudinal extension, in particular over a length of several meters, while the widthwise extension of wires can be approximately 0.5 mm to approximately 6 mm, for example. The image data set is provided to comprise an image of wires of a rope or the rope, in which the longitudinal extension of wires of the rope or the longitudinal direction or longitudinal extension L of the rope coincides substantially with a direction spanning the image plane. Therefore, the image of the wires or the rope in the thus provided image data set also has a longitudinal extension, which, e.g., is longer than the widthwise extension of the image of the wire or the rope in the image data set by a factor greater than 2, preferably greater than approximately 5, and more preferably greater than approximately 10.

The term "wire" in the context of the present invention is not limited to a metal wire, but also comprises plastic fibers used for forming a plastic rope, or natural fibers. The term "wire" as defined in accordance with aspects of the invention thus is to be understood as "wire or fiber, in particular plastic fiber or natural fiber." Accordingly, in addition to wire ropes, the term "rope" also comprises plastic ropes, fiber ropes, etc.

Target values of the pictorial longitudinal extension $J_0$ of the representation of wires can be provided by means of a database, by reading out a data carrier or by means of a user input. The target values of the pictorial longitudinal extension $J_0$ can comprise target points, target positions and/or target directions of the image of wires relative to the pictorial longitudinal extension L of the rope in the image data set. Advantageously, the reference of the target values to the pictorial longitudinal extension L of the rope allows a precise definition of target points, target positions and/or target directions also in the case that the longitudinal extension L of the rope in the image data set does not have a predetermined direction and/or position.

In particular, the target values of the pictorial longitudinal extension $J_0$ of the representation of wires can comprise a wire angle $\beta$ of one or more wires, wherein the wire angle $\beta$ can be defined as the angle that is enclosed between the target value of the pictorial longitudinal extension $L_0$ of the rope and the target value of the longitudinal extension $J_0$ of the wires. Since a defect-free rope can be assumed for the target values, the wire angles $\beta$ can be predetermined for all wires by the type of the rope. For example, the wire angles of adjacent wires can have substantially the same size, that is, adjacent wires are arranged substantially in parallel to each other and are shown substantially in parallel to each other in the image data set.

The target values of the pictorial longitudinal extension $J_0$ of the representation of wires can also comprise an expected target start and/or target end position of one or more wires. The target start and the target end position can define the start and the end, respectively, of the longitudinal extension $J_0$ of the wires visible in the image data set. Alternatively or in addition, the target values can also comprise further target positions of one or more wires of the rope, such as a geometric center or a turning point of the longitudinal extension of the wires visible in the image data set.

The step of determining the spatial extension of the wires in the captured portion of the rope can be performed by adapting an estimated longitudinal extension of the wires to areas of the image data set with high brightness values. For example, a high brightness value is a brightness value that is above the mean value of all brightness values of the image data set relating to the rope.

The determination of the actual pictorial longitudinal extension $J_m$ of the wires in the image data set can be performed by adapting or fitting, in particular by an iterative adaptation or fitting. For the adaptation, the target values of the pictorial longitudinal extension $J_0$ or wires can be assumed as initial starting values for an estimated longitudinal extension. Adapting comprises determining image information of the image data set present at the position of the estimated longitudinal extension, and changing the estimated longitudinal extension to minimize a deviation between the image information present at the estimated longitudinal extension and expected image information. For example, the target values of the pictorial longitudinal extension $J_0$ of the representation of a wire can relate to the wire center line, so that at the points of the image data set where the wire center line is located, for example, higher brightness values can be expected than at the border line between two adjacent wires. Based on the pictorial longitudinal extension $J_0$ according to the target values, the determined actual longitudinal extension $J_m$ can be determined by adapting the estimated longitudinal extension by means of the image data set.

According to the method, on the basis of the provided target values of the pictorial longitudinal extension $J_0$ of the wires and by means of the pictorial longitudinal extension $J_m$ of the wires determined by means of the adaptation, at least one quality value is calculated, which indicates to what extent the actual longitudinal extension $J_m$ deviates from the target value of the pictorial longitudinal extension $J_0$. Therefore, determining the quality value can comprise comparing the determined pictorial longitudinal extension of the wires with the target values of the pictorial longitudinal extension of the wires. The quality value can be determined by means of a quality norm as a function of this comparison, i.e., as a function of the determined pictorial longitudinal extension $J_m$ of the wires and the target values of the pictorial longitudinal extension $J_0$ of the wires. Various distance norms, confidence values, or statistical figures can be used as the quality norm.

On the basis of the at least one determined quality value, pictorial positions within the image data set of the rope, at which at least one quality value exceeds or falls below a predetermined assigned quality threshold value, are discriminated. A potential rope defect can be assigned to the exceeding or falling below of a quality threshold value, so that discriminating can also comprise discriminating with respect to the presence of a rope defect or a specific rope defect.

The result of the discrimination is provided, wherein in addition to the indication that a quality threshold value is exceeded or fallen below within the image data set, the pictorial position assignable or assigned to the exceeding or falling below can be provided as well. Moreover, the pictorial position within the image data set can be linked with a spatial position, so that alternatively or in addition, the spatial positions at which the exceeding or falling below of the quality threshold value occurs can be provided. It is understood that in case the discrimination has been performed with respect to two or more quality threshold values, there can also be provided the information as to which of the quality threshold values was not complied with and in particular which rope defect assigned to the quality threshold values occurred. The provision of the result can in particular comprise the storage on a data carrier, the display on a display device, the printing of a test protocol and the transmission to an external device, for example via an interface in the form of a data stream.

The method can further comprise the steps of: providing target values of the pictorial longitudinal extension $K_0$ of the representation of strands relative to the pictorial longitudinal extension of the rope in the image data set; determining the pictorial longitudinal extension $K_m$ of the strands in the image data set, wherein determining comprises adapting an estimated longitudinal extension to the image data set; determining at least one lay quality value by means of a lay quality norm as a function of the determined pictorial longitudinal extension of the strands and the target values of the pictorial longitudinal extension of the strands.

Objects to be preferably tested are stranded ropes, in particular stranded wire ropes, their strands being arranged around a rope core in a spiral-shaped way. The ropes in turn comprise a strand core around which a plurality of wires is arranged in a spiral-shaped way.

The pictorial longitudinal extension of the representation of strands as defined by the invention is understood such that an image of a strand, which is included in the image data set, extends substantially along a preferred spatial direction, which can be referred to as a longitudinal extension or longitudinal direction of the wire. Just like the wires of a rope, strands extend spatially preferably along their longitudinal extension, in particular over a length of several meters, while the widthwise extension of strands is approximately 1 mm to approximately 30 mm. If the image data set is provided as described above, the longitudinal extension of one of the spiral-like arranged strands coincides at least partially substantially with a direction spanning the image plane.

Target values of the pictorial longitudinal extension $K_0$ of the representation of strands can be provided by means of a database, by reading out a data carrier or by means of a user input. The target values of the pictorial longitudinal extension $K_0$ can comprise target points, target positions and/or target directions of the image of strands relative to the pictorial longitudinal extension L of the rope in the image data set. Advantageously, the reference of the target values to the pictorial longitudinal extension L of the rope allows a precise definition of target points, target positions and/or target directions also in the case that the longitudinal extension L of the rope in the image data set does not have a predetermined direction and/or position.

In particular, the target values of the pictorial longitudinal extension $K_0$ of the representation of strands can comprise a lay angle α of one or more strands, wherein the lay angle α can be defined as the angle that is enclosed between the target value of the pictorial longitudinal extension $L_0$ of the rope and the target value of the longitudinal extension $K_0$ of the strands. Since a defect-free rope can be assumed for the target values, the lay angles α can be predetermined for all wires by the type of the rope. For example, the lay angles of adjacent strands can have substantially the same size, that is, adjacent strands are arranged substantially in parallel to each other and are shown substantially in parallel to each other in the image data set. Alternatively or in addition to the lay angle α, a lay length S of one or more strands can be provided as the target value(s). The lay length S indicates after what distance along the longitudinal direction L of the rope a strand has wrapped the rope core completely. The lay length S can also be determined by means of the strand thickness and the number of strands by a multiplication of the two variables.

The target values of the pictorial longitudinal extension $K_0$ of the representation of strands can also comprise an expected target start and/or target end position of one or more strands or of one or more border lines between adjacent strands. The target start and the target end position can define the start and the end, respectively, of the longitudinal extension $K_0$ of the strands visible in the image data set. Alternatively or in addition, the target values can also comprise further target positions of one or more strands of the rope, such as a geometric center or a turning point of the longitudinal extension of the strands visible in the image data set, or points on the border line of one of the strands with an adjacent strand.

The step of determining the spatial extension of the strands in the captured portion of the rope can be performed by adapting an estimated longitudinal extension $K_m$ of the strands to areas of the image data set with low brightness values. For example, a low brightness value is a brightness value that is below the mean value of all brightness values of the image data set relating to the rope.

The determination of the actual pictorial longitudinal extension $K_m$ of the strands in the image data set is performed by adaptation or fitting, in particular by an iterative adaptation or fitting. For the adaptation, the target values of the pictorial longitudinal extension $K_0$ or strands can be assumed as initial starting values for an estimated longitudinal extension. Adapting comprises determining image information of the image data set present at the position of the estimated longitudinal extension, and changing the estimated longitudinal extension to minimize a deviation between the image information present at the estimated longitudinal extension and expected image information. For example, the target values of the pictorial longitudinal extension $K_0$ of the representation of a strand can relate to the border line of this strand with an adjacent strand, so that at the points of the image data set where the border line of the strand is located, lower brightness values than at the areas surrounding the border line can be expected due to shadows. Based on the pictorial longitudinal extension $K_0$ according to the target values, the actual longitudinal extension $K_m$ can be determined by adapting the estimated longitudinal extension by means of the image data set.

According to various embodiments of the method, on the basis of the provided target values of the pictorial longitudinal extension $K_0$ of the strands and by means of the pictorial longitudinal extension $K_m$ of the strands determined by means of the adaptation, the lay quality value $G_S$ can be calculated. The lay quality value $G_S$ indicates to what extent the actual longitudinal extension $K_m$ deviates from the target value of the pictorial longitudinal extension $K_0$, for example by a variation of the lay length S or of the lay angle α. Determining the lay quality value $G_S$ can comprise comparing the determined pictorial longitudinal extension of the strands with the target values of the pictorial longitudinal extension of the strands. The lay quality value $G_S$ can be determined by means of the lay quality norm as a function of this comparison, i.e., as a function of the determined pictorial longitudinal extension $K_m$ of the strands and the target values of the pictorial longitudinal extension $K_0$ of the strands. Various distance norms, confidence values, or statistical figures can be used as the lay quality norm.

Target values of the pictorial longitudinal extension $J_0$ of the representation of wires can be provided relative to the pictorial longitudinal extension of the strands in the image data set. Further, the pictorial longitudinal extension $J_m$ of the wires in the image data set can be determined relative to the determined longitudinal extension of the strands.

As has been explained above, the provided target values of the pictorial longitudinal extension $J_0$ of the representation of wires, for example target points, target positions and/or target directions of the image of wires, can be indicated relative to the pictorial longitudinal extension L of the rope in the image data set. In the preferred case of a test of a stranded rope, these target values of the longitudinal extension $J_0$ can be indicated alternatively or in addition relative to a target value of the longitudinal extension $K_0$ of one or more strands. Advantageously, the reference of the target values to the pictorial longitudinal extension $K_0$ of the strand allows a precise definition of target points, target positions and/or target directions also in the case that the actual longitudinal extension $K_0$ of the strand relative to the longitudinal extension L of the rope in the image data set does not have a predetermined direction and/or position. Advantageously, this allows distinguishing in particular between cases in which a strand as a whole is not located in the target position, but the longitudinal extension of the wires within the strand corresponds to its target positions, and cases in which deviations in the longitudinal extension of the wires with respect to the target values occur.

In particular, the target values of the pictorial longitudinal extension $J_0$ of the representation of wires can comprise a wire-strand-angle γ of one or more wires, wherein the wire-strand-angle γ can be defined as the angle that is enclosed between the target value of the pictorial longitudinal extension $K_0$ of the strand and the target value of the longitudinal extension $J_0$ of the wires. For a defect-free strand, the wire-strand-angles can be constant preferably for all wires, i.e., the adjacent wires are arranged substantially in parallel with each other.

The at least one quality value can comprise a geometry quality value $G_G$, which can be determined by means of a geometry quality norm as a function of a geometric distance between the determined pictorial longitudinal extension $J_m$ of the wires and the target values of the pictorial longitudinal extension $J_0$ of the wires, and/or as a function of a geometric distance between the determined pictorial longitudinal extensions $J_m$ of at least two adjacent wires.

The geometry quality value $G_G$ can be calculated on the basis of the provided target values of the pictorial longitudinal extension $J_0$ of the wires and the actual pictorial longitudinal extension $J_m$ of the wires determined by means of the adaptation. The geometry quality value $G_G$ preferably indicates to what extent the actual longitudinal extension $J_m$ deviates from the target value of the pictorial longitudinal extension $J_0$. The geometry quality value $G_G$ can for example be determined by determining a Euclidean distance as the preferred geometry quality norm between the two longitudinal extensions and/or between marked points with the two longitudinal extensions. Alternatively or in addition, the geometry quality norm can also comprise a difference of the wire angle according to one of the target values and a determined actual wire angle.

The geometry quality value $G_G$ can preferably also indicate the extent of the deviation of the actual longitudinal extension $J_m$ of two adjacent wires from each other or from a corresponding target value of the pictorial longitudinal extension $J_0$. The geometry quality value $G_G$ can for example comprise a difference of the determined wire angles according to the determined actual longitudinal extension $J_m$ of two or more adjacent wires. A variation of the wire angle can for example be indicative of a displacement or shift of two adjacent wires.

The method can further comprise the step of determining a brightness distribution function along the determined pictorial longitudinal extension of the wires, wherein the at least one determined quality value comprises a continuity quality value $G_S$, which is determined by means of a continuity quality norm as a function of the brightness distribution function, the first derivative of the brightness distribution function and/or the second derivative of the brightness distribution function and/or their nth-order moments with n=0, 1, 2.

The determined pictorial longitudinal extension $J_m$ of one of the wires can be parameterized by a continuous line between two end points. Further, the continuous line can be selected such that the course of the line substantially coincides with the center line along the wire. One of the values included in the image data set, for example the brightness value of the image, is determined along the line or along a band having a predetermined width, in which the line is located, so that the brightness distribution function along the line results therefrom.

The resulting brightness distribution function of defect-free wires can be a substantially constant function, which can be characterized by a mean value of the brightness values. A defective point of the wire can lead to a variation of the brightness distribution function. For example, a breakage of the wire can lead to a change of the mean value of the brightness distribution function at intervals. In other words, the brightness distribution function can include an interval at which the brightness distribution function has lower values, for example values reduced by 50 percent with respect to the values within an environment of the interval or values close to zero. These exemplary deviations can be characterized by the first and/or the second statistical moment. The continuity quality value can comprise the variance or the mean variance of the brightness distribution function.

As a further example, notches or local damages (e.g. by lightning stroke) in the wire can lead to an irregular brightness distribution function. Such irregularities can for example lead to changes in the first and/or the second derivative of the brightness distribution function at intervals, which changes are characterized by a local change of the mean value in the first or second derivative, respectively. These changes in the derivatives can preferably be characterized by the first and/or the second statistical moment of the respective derivative. The continuity quality value can comprise the variance or the mean variance of the first or second derivative of the brightness distribution function.

Particularly, a deviation of the determined brightness distribution function from an expected target distribution of the brightness distribution function can be characterized by means of a continuity quality norm, which is calculated on the basis of the mean value and/or the variance of the brightness distribution function, the first derivative of the brightness distribution function and/or the second derivative of the brightness distribution function. For example, the continuity quality norm can comprise a weighted sum of the mean values and/or variances of the brightness distribution function or the derivatives thereof.

The method can further comprise the steps of: determining the local pictorial diameter $D_m$ of the rope in the image data set; providing target values of the local diameter $D_0$; and determining a diameter quality value by means of a diameter quality norm as a function of the determined pictorial diameter $D_m$ and the target values of the local diameter $D_0$.

The local pictorial diameter $D_m$ of the rope can be limited to a portion along the longitudinal extension of the rope in the image data set, for example, to a length of approximately 20 or approximately 100 image points, or to a corresponding length of the actual rope of approximately 10 mm or approximately 50 mm.

The local diameter $D_m$ is determined along a diameter direction perpendicular to the longitudinal extension or longitudinal direction L of the rope. The diameter can be determined by a distance determination of two envelops of the rope, which extend along the longitudinal extension or longitudinal direction L. The envelops can, for example, be determined by a Hilbert transform of the two rope contour lines.

The provided target value of the local diameter $D_0$ can be constant over the entire rope length. The diameter quality value $G_D$ can be calculated on the basis of the provided target value(s) and the determined actual local diameter $D_m$ of the diameter quality value $G_D$. The diameter quality value $G_D$ preferably indicates to what extent the actual local diameter $D_m$ deviates from the target value of the diameter $D_0$, for example by means of the Euclidean distance between the two diameter values as the preferred diameter quality norm. A variation of the diameter quality value $G_D$ can for example be indicative of an expansion or a collapse of the rope.

The step of providing target values of the spatial extension of the strands and/or the spatial extension of the wires can comprise the following steps: selecting an image data set; determining at least two support points and a connection line defined by the support points such that the connection line substantially coincides with a border line between two adjacent strands, or a border line between two adjacent wires, or a center line of a strand, or a center line of one of the wires; and storing the support points on a storage medium.

The target values can be determined by means of a selected, in particular, representative image data set. Further preferably, one or more target values can be determined on the basis of rope-specific manufacturer's data, for example on the basis of a numerical rope model and the rope-specific characteristic parameters, such as rope diameter, number of strands, strand diameter, type of twist, wire strength, number of wires, diameter of the rope core, diameter of the strand core, etc.

At least two or more support points, by which a connection line is defined, can be determined. The number of support points can be 2, 3, 4, 5, 6, 7 or a different natural number. The connection line can be specified between the support points by a linear or cubic interpolation. Moreover, a spline can connect the support points with each other as a connection line. However, the support points can also define a regression line or a regression polynomial, or another regression function, wherein the support points do not have to be on the regression function.

The support points can be positioned with respect to the image data set such that the connection line defined by the support points coincides with a border line between two adjacent strands or with a border line between two adjacent wires or with a center line of a strand or with a center line of a wire. A thus determined connection line can characterize the longitudinal extension of a wire and/or of a strand, and can be used as an initial starting value for adapting and determining an actual longitudinal extension.

In order to make the support points or the connection line(s) available as target values for the test method, the support points and/or the connection lines can preferably be transferred to a storage medium.

The method can further comprise the step of assigning the quality value to the associated, discriminated, spatial positions along the rope. Advantageously, rope portions having a potential, determined rope defect can be detected quickly, in particular to perform a visual check of these rope portions on the rope itself and/or by means of the pictorial representation of the rope.

Further, the method can comprise the step of assigning an assessment feature, in particular on the basis of the at least one quality value, to the associated, discriminated, spatial positions along the rope. Exemplary assessment features can comprise classifications of the possible rope defects, such as "wire breakage," "strand shift," "notch," "lightning stroke," etc. The assessment feature could also comprise a score value indicative of the severity of a defect or the determination reliability. In particular, one or more assessment features can be included in an error log in order to advantageously enable a user of the method in a simple way to see the determined rope defects.

Another aspect of the present invention relates to a computer program product, in particular embodied as a signal and/or as a data stream, which comprises computer-readable instructions, wherein the instructions perform a method according to aspects of the invention, in particular as described above, when loaded and executed on a suitable computer system. In other words, a computer program product is provided, which comprises program parts for performing the method according to aspects of the invention or a preferred embodiment thereof. Moreover, a computer program is provided, which, when loaded on a computer, can perform the method according to aspects of the invention or a preferred embodiment thereof. Further, a computer-readable storage medium is provided, on which such a computer program is stored.

Yet another aspect of the invention relates to a system for the optical testing of a rope. The system comprises: at least one image data capturing device adapted to optically capture at least one portion of the rope; a target value storage unit adapted to provide target values of the longitudinal extension $K_0$ of the strands and/or of the longitudinal extension $J_0$ of the wires, in particular relative to the longitudinal extension $K_0$ of the strands, to a discriminating unit; an image data evaluating device adapted to determine a longitudinal extension $K_m$ of the strands in the captured portion of the rope and/or the longitudinal extension $J_m$ of the wires in the captured portion of the rope, in particular relative to the determined longitudinal extension $K_m$ of the strands; a discriminating unit adapted to determine at least one quality value by means of a quality norm as a function of the determined longitudinal extension $J_m$ of the wires and the target values of the longitudinal extension $J_0$ of the wires and/or at least one quality value by means of a quality norm as a function of the determined longitudinal extension $K_m$ of the strands and the target values of the longitudinal extension $K_0$ of the strands, as well as to discriminate the pictorial positions within the image data set of the rope, at which at least one quality value exceeds or falls below a predetermined, assigned quality threshold value; and an output unit.

The discriminating unit can be adapted to perform the assignment of the quality value to the associated, discriminated, spatial positions along the rope.

The system can comprise a rope assessment unit adapted to assign an assessment feature to the pictorial or spatial positions along the rope, which are discriminated by the discriminating unit.

Advantageously, a human inspector can be informed of all potential rope defects and their positions by means of a log output by the output unit. Advantageously, a visual check can be reduced to a fraction of the entire rope length when implementing the system, according to aspects of the invention. Further advantageously, the rope test is also improved in terms of safety at work for the competent inspector.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings:

FIG. 6 is an exemplary embodiment of obtained target values;

DETAILED DESCRIPTION OF PREFERRED EMBODIMENTS

Various exemplary embodiments will be described more fully hereinafter with reference to the accompanying drawings, in which some exemplary embodiments are shown. The present inventive concept may, however, be embodied in many different forms and should not be construed as limited to the exemplary embodiments set forth herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device may be otherwise oriented (e.g., rotated 90 degrees or at other orientations) and the spatially relative descriptors used herein interpreted accordingly.

Figure 1:
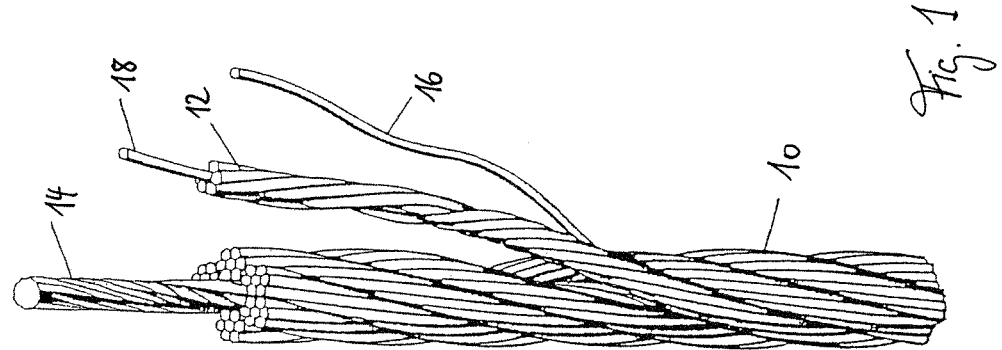
FIG. 1 shows a stranded rope as an exemplary rope.

As a preferred rope 10, FIG. 1 shows a stranded rope 10 as an exemplary wire rope. Stranded ropes 10 comprise several strands 12, which are wound helically around a rope core 14. The strands 12 are comprised of one or more layers of wires 16, which are wound or stranded or laid helically around a strand core 18. The common term "lay" is used synonymously with the term "stranded" in the following. The strand core 18 can be comprised of a plastic fiber or a wire, for example. Preferably, the strands 12 are formed of wires and a strand core 18 having a similar, preferably with a substantially same diameter. Further preferably, six wires 16 are arranged around the strand core 18 to form the strand 12. The rope strand 14 can be made of non-woven fabrics, in particular of plastics, or of at least one wire, or in turn be formed as a strand or rope. Preferably, the stranded rope 10 is formed of strands 12 and a rope core 14 having a similar, preferably with a substantially same diameter. Further preferably, four to ten strands 12 are arranged around the rope core 14 to form the rope 10. In the illustrated, particularly preferred embodiment, six strands 12 are arranged around the rope core 14.

Ropes or stranded ropes 10 of the type shown in FIG. 1 are used as moving ropes, stationary ropes, or track ropes in various fields of technology. "Moving ropes" are ropes that move over driving pulleys, rope pulleys, and drums, and in doing so adapt the curvature thereof, e.g. hoisting ropes, tie ropes, block lines of cranes, elevator ropes, scraper ropes, and hauling ropes for cableways. "Stationary ropes", also called anchor cables or standing ropes, are understood to be ropes that do not move over rope pulleys and the ends of which are supported in fixed points, for example stay ropes for masts and jibs and guide ropes for elevators and winding apparatuses as well as anchor moorings for dredgers with and without anchor windlasses. Track ropes are ropes on which rollers of conveying means move, for example, such as conveying means of cableways, cable cranes, and cable scrapers. Track ropes fulfill a similar function as guide rails. The radius of curvature of a track rope below the roller is larger than the roller radius. It is understood that the different ropes can be made of different materials depending on the application, for example of plastics such as aramid, Dyneema, polyamide, or steal, stainless steel, or galvanized steel.

Figure 2:
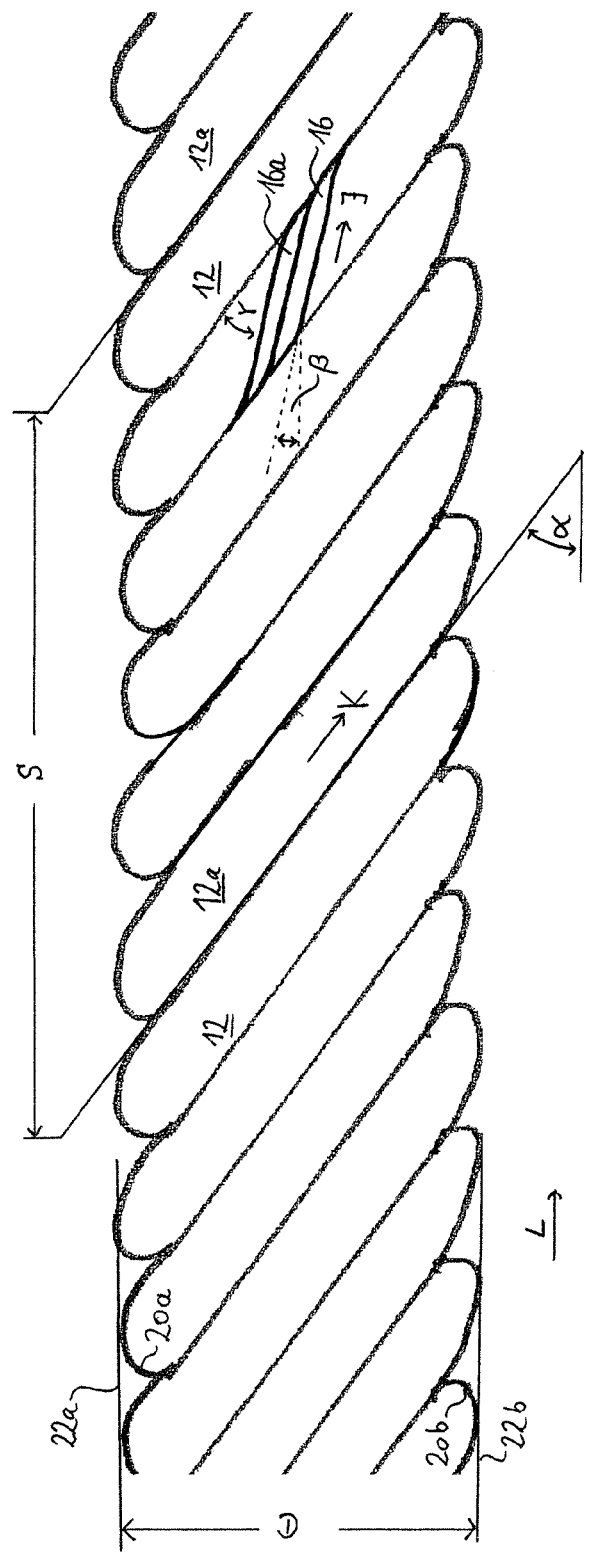
FIG. 2 provides characteristic construction parameters of a stranded rope.

All rope types have specific, unique construction patterns that can be recognized in a digital image analysis. FIG. 2 illustrates the characteristic construction parameters of a stranded rope 10. The diameter D of the stranded rope 10 is measured perpendicularly to a longitudinal direction L of the stranded rope 10. Preferably, the diameter D can be measured by optically capturing the stranded rope 10 and by a subsequent distance determination of the two envelopes 22a, 22b of the associated, captured stranded rope contour lines 20a, 20b, the envelopes extending along the longitudinal direction L. The envelopes 22a, 22b can be determined by a Hilbert transform of the captured stranded rope contour lines 20a, 20b, for example.

Further characteristic parameters of the stranded rope 10 are the lay length S and the lay angle $\alpha$ of the strands 12, 12a with respect to the longitudinal direction L. The lay length S describes in what distance along the longitudinal direction L of the rope 10 a strand 12 has wrapped the rope core 14 completely. The lay angle $\alpha$ can be defined as the angle that is enclosed between the longitudinal direction L of the rope 10 and the longitudinal direction K of the strand 12. For a defect-free rope, the longitudinal direction K of two adjacent strands 12, 12a is parallel to each other, so that the lay angle $\alpha$ can be used as a characteristic parameter for all strands 12, 12a.

A further characteristic variable of the stranded rope 10 is the wire angle $\beta$ of the individual wires 16, 16a with respect to the longitudinal direction L of the rope 10. The wire angle $\beta$ can be defined as the angle that is enclosed between the longitudinal direction L of the rope 10 and the longitudinal direction J of the wires 16, 16a. For a defect-free rope, the longitudinal direction J of two adjacent wires 16, 16a is substantially parallel in sections. That is, the adjacent wires 16, 16a are wound around the strand core in an adjacent, in particular mechanically contacting way. The wire angle $\beta$ can therefore be used as a characteristic variable for all wires 16, 16a.

Figure 3:
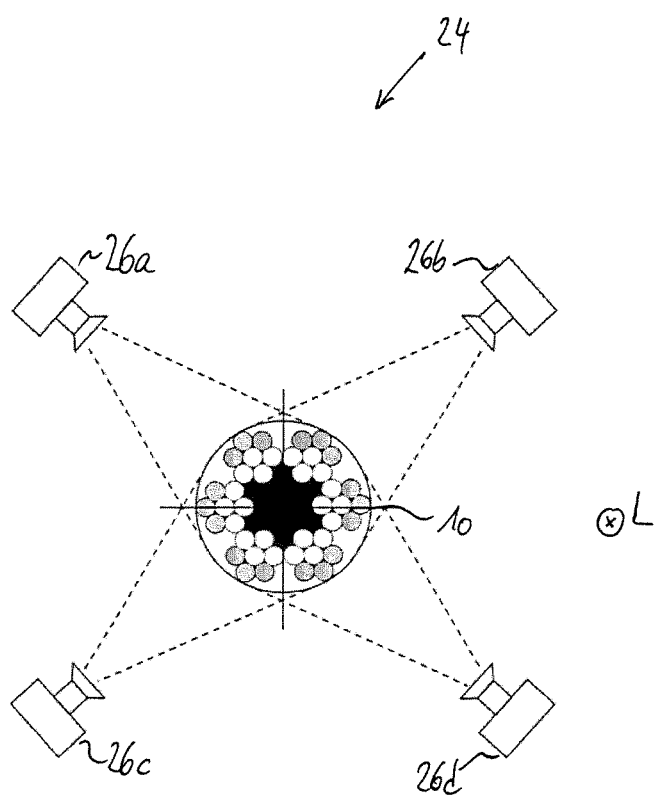
FIG. 3 is a schematic of an embodiment of a preferred image data capturing device, in accordance with aspects of the invention.

FIG. 3 shows a schematic image data capturing device 24 adapted to capture a rope 10 in an image data set. In a preferred embodiment 3 to 5, in particular 4, the image data capturing device 24 comprises cameras 26a-26d, which are arranged in a plane perpendicular to the longitudinal direction L of the rope 10. The cameras 26a-26d are preferably line scan cameras or CCD (charge-coupled device) cameras. Each of the cameras 26a-26d covers an associated quadrant of approximately 90 degrees of the outside surface of the rope, so that an image data set that fully includes the outside surface of the rope can be provided. The rope 10 can be shifted relative to the image data capturing device 24 along or opposite to the longitudinal direction L. It is understood that in the case of a stationary rope, the image data capturing device 24 can be shifted as well. In this embodiment, preferably, the relative speed between the rope 10 and the cameras 26a-26d can be up to 5 m/s, in various embodiments.

In this embodiment, preferably, the cameras 26a-26d are displaceable within the image data capturing device 24 relative to the rope in order to adapt the image data capturing device 24 to the diameter of the rope to be tested. The illumination of the rope 10 can preferably be accomplished with artificial light sources, which allow an improved contrast in the image data set In particular, the image data capturing device 24 can have high-performance LEDs (light emitting diodes) as a light source.

Figure 3A:
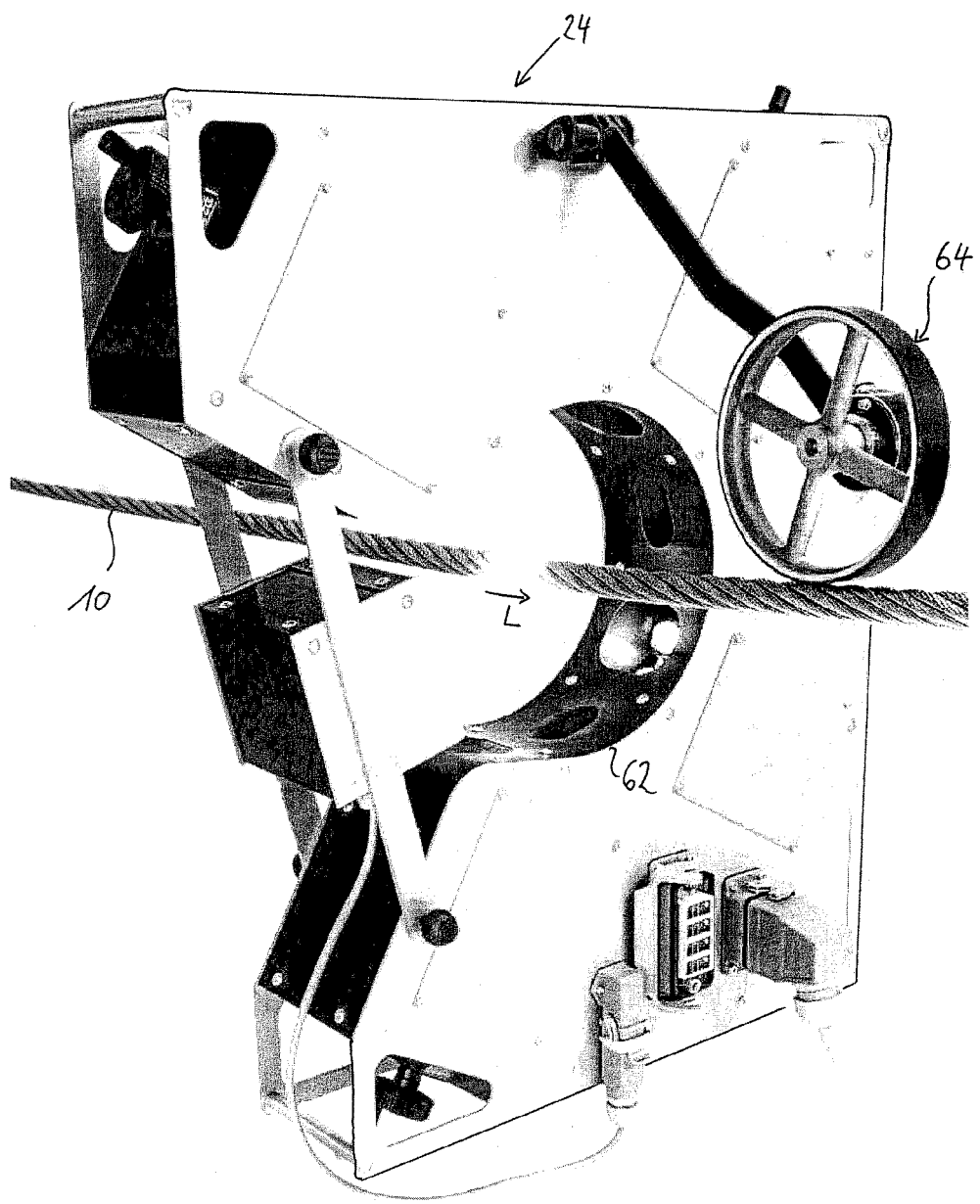
FIG. 3a shows an embodiment of a preferred image data capturing device, in accordance with aspects of the invention.

FIG. 3a shows an image data capturing device 24 adapted to capture a rope 10 in an image data set. In the preferred embodiment 4, the image data capturing device 24 comprises cameras (not shown), which are arranged in a plane perpendicular to the longitudinal direction L of the rope 10 around a rope passage opening 62 of the image data capturing device 24. The rope 10 can be shifted through the rope passage opening 62 relative to the image data capturing device 24 along or opposite to the longitudinal direction L. It is understood that in the case of a stationary rope, the image data capturing device 24 can be shifted as well. Further preferably, the image data capturing device 24 has a rope feed measuring device 64, which can measure or detect the length of the rope 10 displaced along or opposite to the longitudinal direction L. In particular, a measuring wheel 64 can be provided as a preferred rope feed measuring device 64, which is in frictional contact with the rope and is therefore rotated by the feed of the rope 10. A pulse generator can be connected with the measuring wheel 64, for example, so that a rotation of the measuring wheel 64 by a predetermined angle generates are recordable pulse. The number of pulses can be recorded or counted during the feed of the rope 10 and be assigned to individual images of the image data set. Advantageously, it is possible by means of the rope feed measuring device 64 or the measuring wheel 64 to assign captured image data or part of the image data set to a geometric position along the rope 10.

Figure 4:
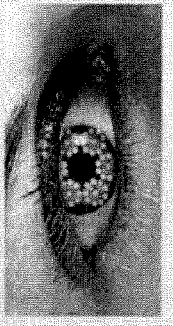
FIG. 4 is an embodiment of a display screen generated by a preferred step of obtaining rope-specific target values, in accordance with aspects of the invention.

FIG. 4 shows a step of obtaining rope-specific target values by means of a data input mask 28. For example, the data input mask 28 comprises the lay length $S_0$ indicated by manufacturer as well as the target value of the diameter $D_0$. The actual values of the diameter $D_m$ and the lay length $S_m$, which are determined on the basis of a representative rope portion, can be input and used as a comparative value for the determination of deviations with respect to the local diameter and the lay length.

Figure 5:
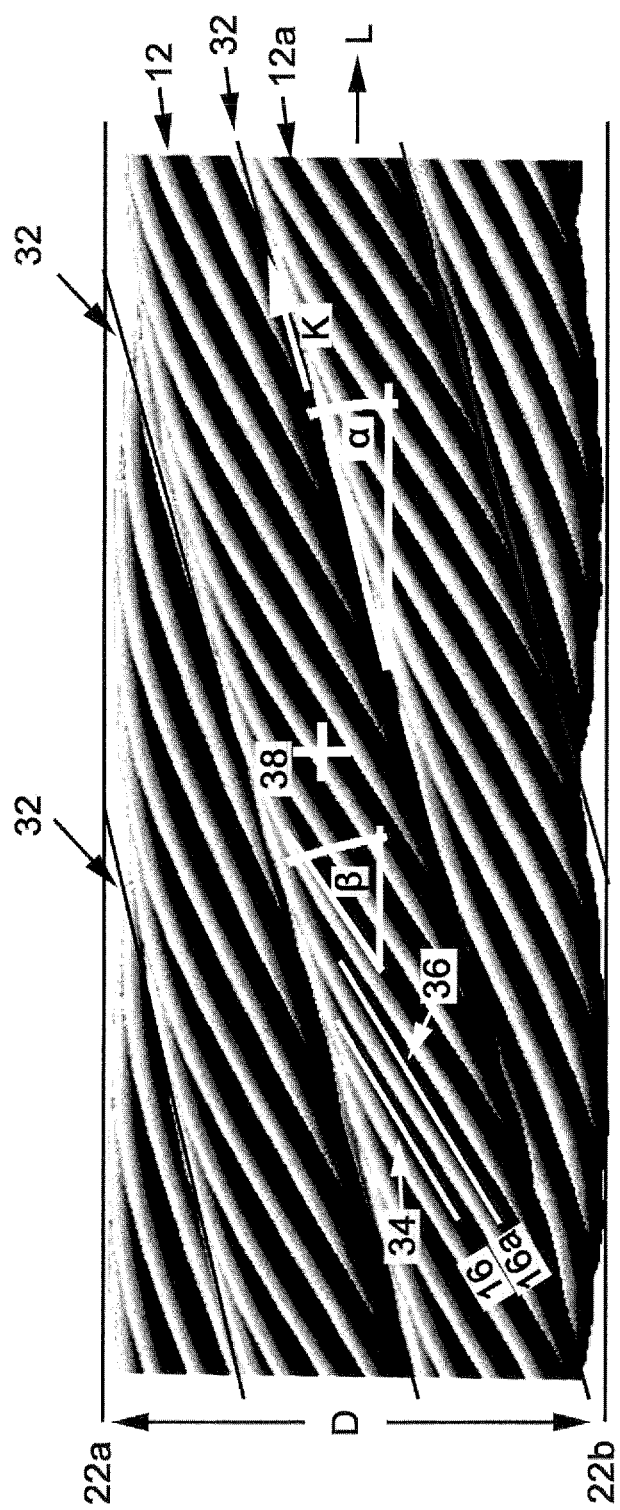
FIG. 5 is an embodiment of a preferred step of obtaining rope-specific target values, in accordance with aspects of the invention.

FIG. 5 shows a further step of obtaining rope-specific target values by means of an image data set including a rope portion 30. The envelopes 22a, 22b of the rope portion 30 can be specified manually or automatically, with the help of which the longitudinal extension L of the rope portion 30 and the diameter $D_m$ in the rope portion can be determined. Moreover, two support points can further be specified, for example, by a user, for example, by actuating an operating element of a display device representing the rope portion 30, wherein the support points define a straight connection line or lay line 32 such that the connection line corresponds to the border line between two adjacent strands 12, 12a. This step can be performed for several border lines between several strands. By means of at least a determined connection or lay line 32, which is parallel to the longitudinal direction K of the strand 12, the lay angle α can be determined relative to the longitudinal direction or longitudinal extension L of the rope portion 30. Further, a reference point 38 can be determined, which is arranged substantially in a centered way between two lay lines 32 and can be used as a reference for the center of the strand 12, for example to determine the support points for the target values of the individual wires 16, 16a relative to this reference point, i.e. relative to the strand 12.

Further support points can be specified correspondingly, which define a substantially straight connection line or wire border line 34 such that the connection corresponds to the border line between two adjacent wires 16, 16a. Further, support points can be specified, preferably by a user, which define a substantially straight connection line or wire line 36 such that the connection line substantially corresponds to the center line of a wire 16a. The wire angle β relative to the longitudinal direction or longitudinal extension L of the rope portion 30 can be determined by means of the wire border line 34 and/or the wire line 36.

FIG. 6 shows the target values determined as described with reference to FIG. 5.

Figure 7:
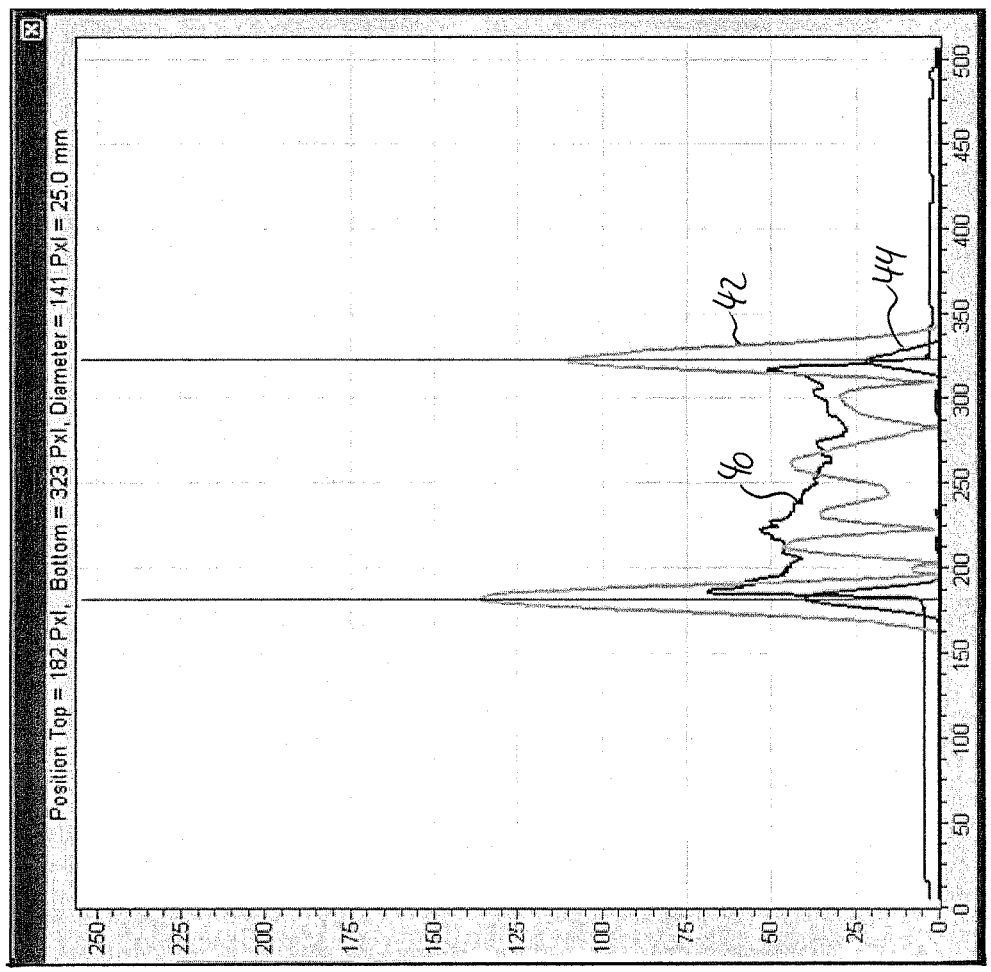
FIG. 7 is an embodiment of a preferred plot generated from automatic determination of the local diameter of the rope, in accordance with aspects of the invention.
Figure 7A:
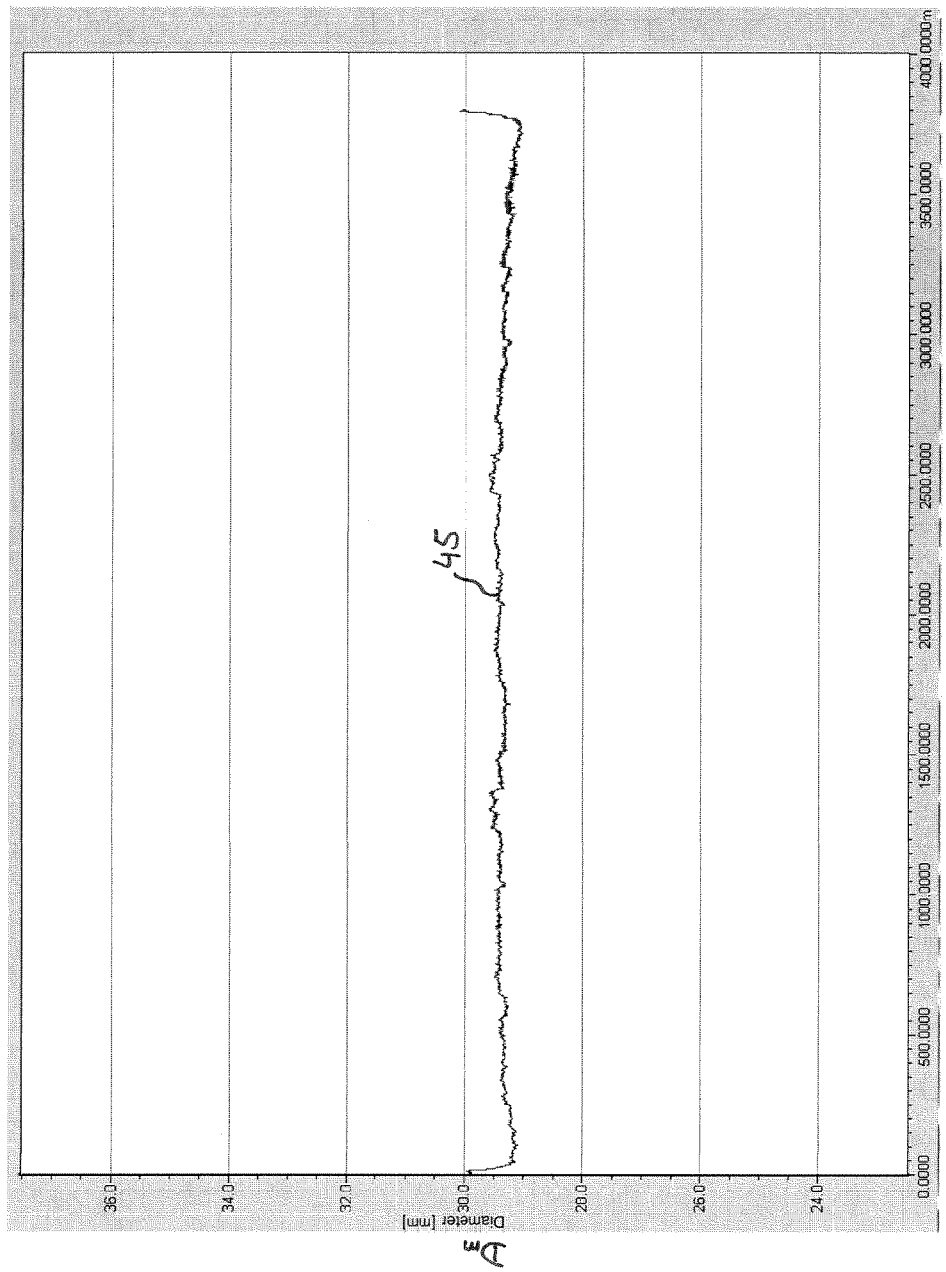
FIG. 7a is an exemplary embodiment of a plot of determined local diameters of the rope, in accordance with aspects of the invention.

FIG. 7 shows an automatic determination of the local pictorial diameter $D_m$ of the rope in the image data set. Preferably, the determination of the local diameter $D_m$ can be performed by means of edge detection, preferably on the basis of a smoothed image data set. For example, the determination of the local diameter $D_m$ can be performed on the basis of a diameter correlation (illustrated in FIG. 7 as a curve with the reference numeral 40), a calculated entropy (illustrated in FIG. 7 as a curve with the reference numeral 42) and/or edge detection (illustrated in FIG. 7 as a curve with the reference numeral 44). The resulting local diameter $D_m$ can be plotted against the rope length, as is shown in FIG. 7a (illustrated as a curve with the reference numerals 45).

Figure 8:
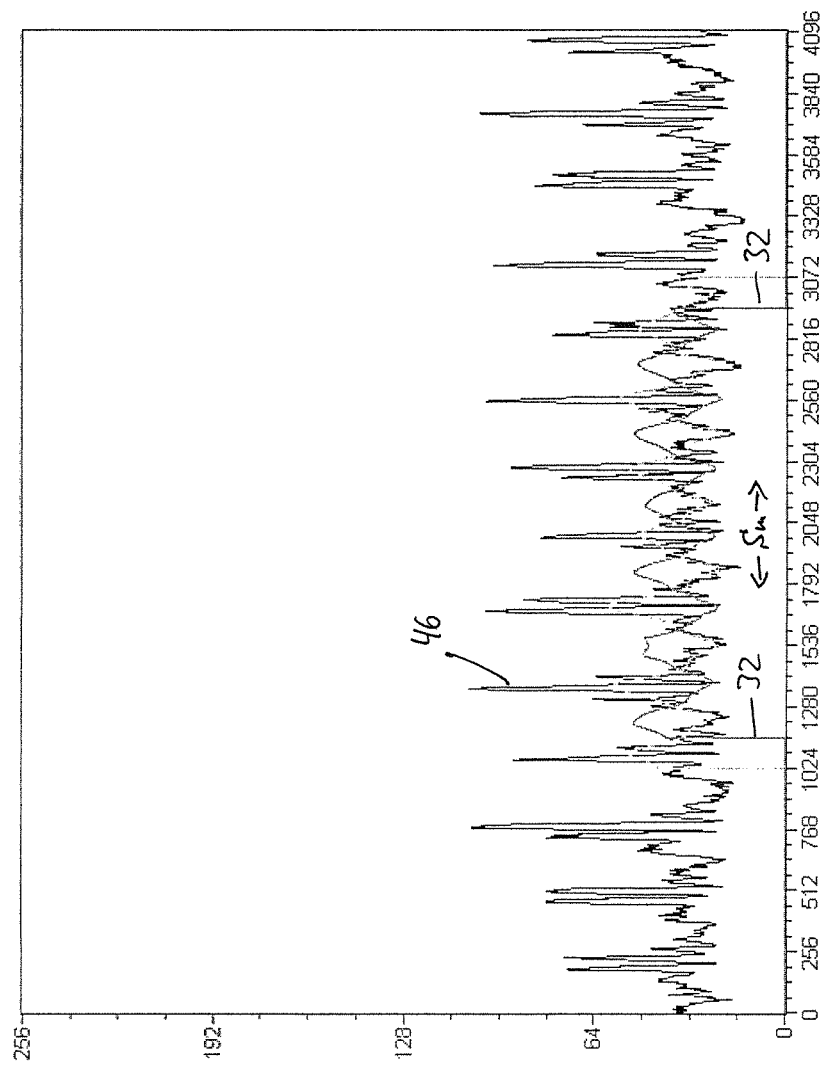
FIG. 8 is an embodiment of a plot of a preferred automatic determination of the lay length, in accordance with aspects of the invention.

FIG. 8 shows an automatic determination of the lay length in the image data set, i.e. of a localized lay length $S_m$. Preferably, the determination of the lay length $S_m$ can be performed based on the evaluation of the brightness values of the image data set along the longitudinal direction or longitudinal extension of the rope or the rope portion (illustrated in FIG. 7 as a curve with the reference numeral 46). To eliminate the effect of linear shifts, a transformation in the Fourier space can be performed, wherein the spatial wave numbers are not localized any more and a shift of the rope along the longitudinal direction L does not influence the result. To determine the lay length, the number of strands, e.g. 6, and the previously obtained actual lay length (see FIG. 4) can be used. The lay length $S_m$ can be determined by multiplying the values number of strands and strand width.

The position of border lines of two adjacent strands, i.e. the lay line 32, can be determined by cross correlation with a known strand structure, as it can be obtained in the determination of the target values, for example. The border lines are usually characterized by clearly defined areas with low brightness values, since usually much shadow occurs between two strands.

Figure 8A:
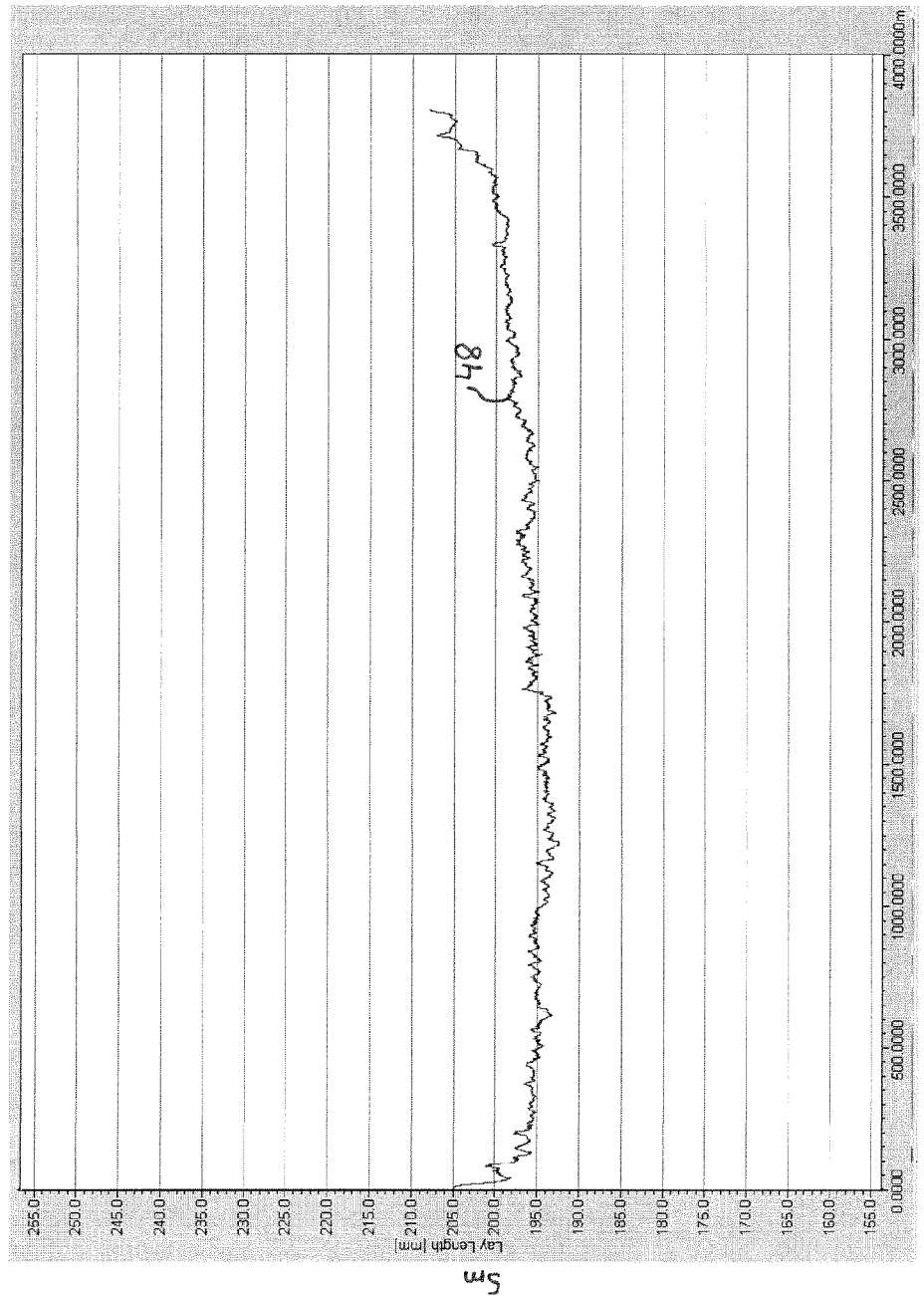
FIG. 8a is an exemplary embodiment of a plot of determined local lay length of the rope, in accordance with aspects of the invention.

The determined local lay length Sm can be plotted against the rope length, as is shown in FIG. 8a (illustrated as a curve with the reference numeral 48). In addition to the lay length $S_m$, the strand center can further determined as a reference point for further steps of the test method.

Figure 9:
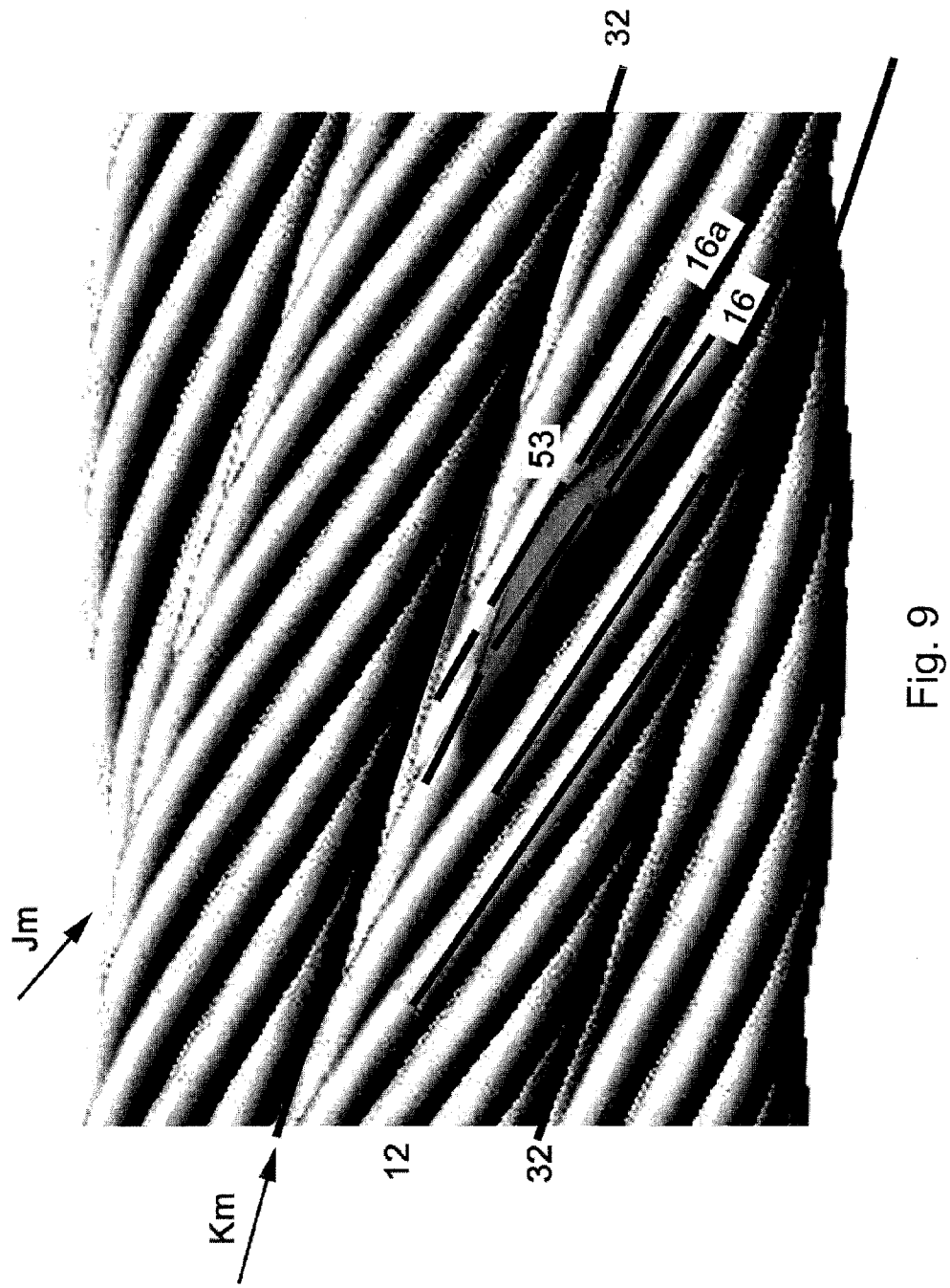
FIG. 9 is an embodiment of an automatic detection of wire shifts or wire shifts in an image data set, in accordance with aspects of the invention.

FIG. 9 schematically shows the automatic detection of wire shifts or wire shifts in an image data set. In a preferred embodiment of the test method, it is determined with the help of the geometry quality value $G_G$ to what extent the actual longitudinal extension $J_m$ of a wire 16 deviates from the target value of the pictorial longitudinal extension $J_0$. In the shown embodiment of this method, the target value of the longitudinal extension $J_0$ is defined relative to the longitudinal extension $K_m$ of the strand 12, which is parallel to the lay line 32. The geometry quality value $G_G$ is preferably defined as an adaptation error with respect to an adaptation by means of a straight line. As is shown in FIG. 9, it is difficult to adapt the wire 16 at a shift location 53 by means of a straight line. Therefore, the wire shift can be detected at this location. Alternatively or in addition, a specific variation of the longitudinal extension between adjacent wires 16, 16a can also be indicative of a shift or shift of two adjacent wires 16, 16a.

Figure 10:
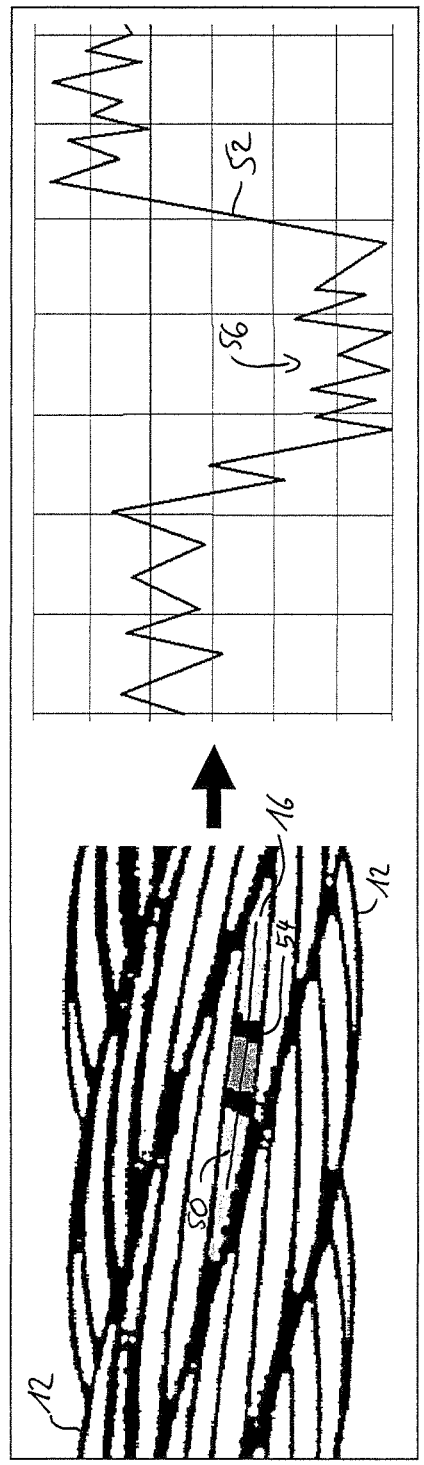
FIG. 10 is an embodiment of a preferred detection of wire breakages, in accordance with aspects of the invention.

FIG. 10 schematically shows the automation detection of wire breakage in an image data set. In an embodiment of the test method, as is described with reference to FIG. 8, the strand center 38 is calculated on the basis of the detected strand borders or lay lines 32. At the strand center 38 are aligned the previously obtained target values for the longitudinal extension $J_0$ of the wires 16, which are part of the strand 12. By means of an adaptation, in particular an iterative adaptation, the actual longitudinal extensions $J_m$ of the wires 16 are determined. Target values representing a center line of a wire are adapted such that these center lines or wire lines follow the brightest possible locations of the image data set. Target values representing a border line between two adjacent wires are adapted such that these border lines follow the darkest possible locations of the image data set. As a further boundary condition of the adaptation it may be provided that adjacent support points of wires and border lines between wires displace each other, i.e., assume a maximum distance to each other. To perform the adaptation, the optimization of a multi-dimensional cost function is necessary, for example.

Now, for every identifiable or sufficiently resolvable wire 16, the brightness value of the image can be obtained along an associated, adapted continuous line 50, which represents the longitudinal extension $J_m$ of the wire 16, so that a brightness distribution function 52 along the line 50 results therefrom. In the example shown in FIG. 9, a break 54 of the wire 16 leads to a variation of the brightness distribution function 52, so that the brightness distribution function 52 has a reduced local mean value in an interval 56.

Changed local mean values of the brightness distribution function 52 can be evaluated automatically by means of a continuity quality norm $G_S$, so that brightness value changes along a line 50 (bright-dark, dark-bright) lead to the continuity quality value being exceeded and thus to a defect detection. It is understood that the above-described method can also be applied to the border lines between two wires 16 and is preferably used in addition.

Figure 11:
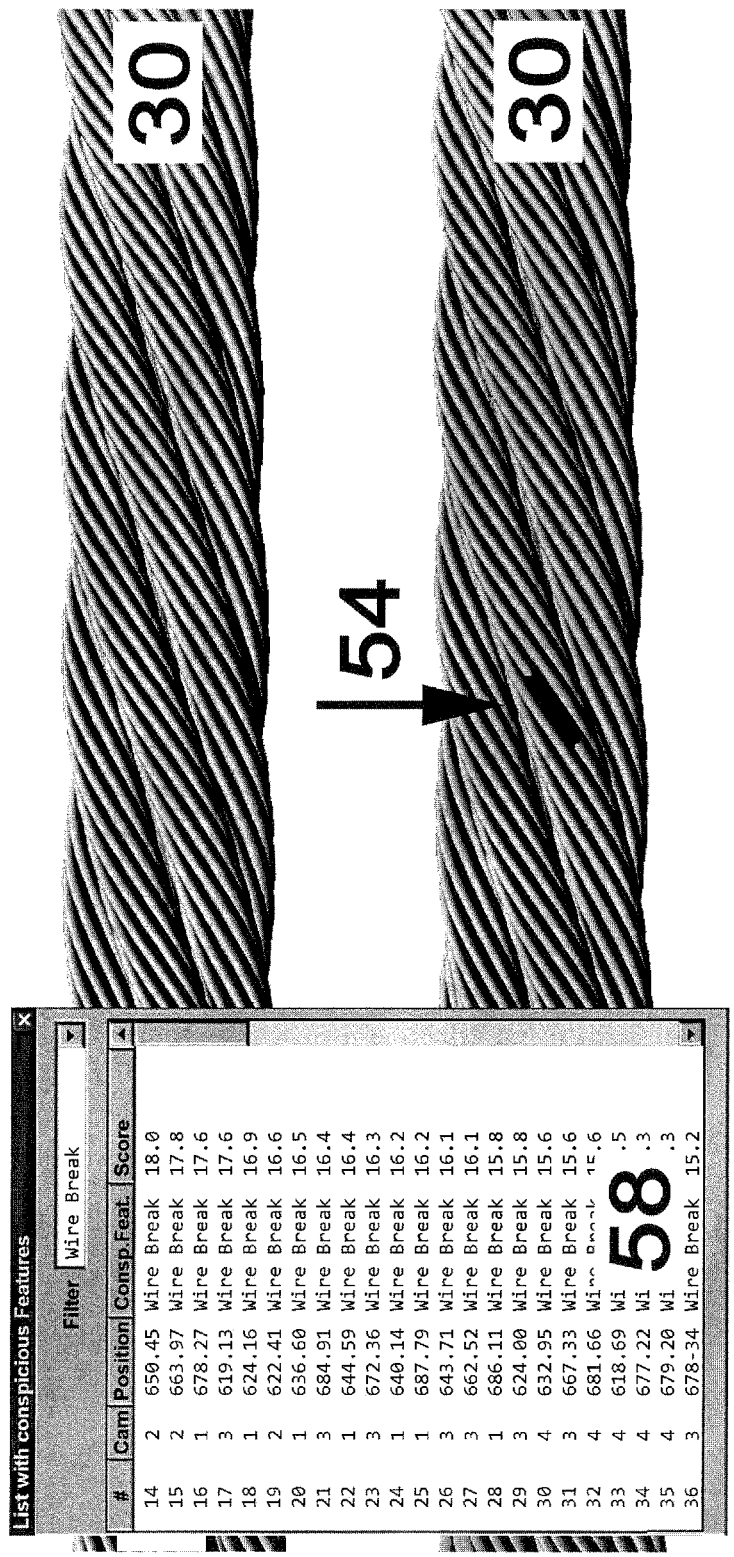
FIG. 11 is an exemplary embodiment of an output of a result of the test method, in accordance with aspects of the invention.

FIG. 11 shows the result of the test method. According to the obtained quality values on the basis of the associated quality norms, which each constitute a benchmark for an associated rope defect, conspicuous rope portions have been discriminated and listed in an error log 58 together with the corresponding rope position and the determined rope defect. Preferably, the computer program performing the method according to aspects of the invention establishes a link between the elements of the error log 58 and, in particular full, a pictorial representation 60 of the rope portion 30 having the defect (for example, a wire breakage 54). Advantageously, a human tester can check or verify all potential rope defects visually on the basis of the pictorial representation without actually looking at the rope portion. Advantageously, the test method can be performed remote from the place of use of the rope. Further advantageously, the visual check or verification can be limited to the automatically discriminated rope portions 30, so that approximately 90 percent of a rope does not require an inspection by a human tester. Further preferably, the test method and the assessment of the discriminated rope defects can be performed automatically.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

LIST OF REFERENCE NUMERALS 10 rope or stranded rope
12, 12a strand
14 rope core
16 wire
18 strand core
20a, 20b stranded rope contour line
22a, 22b envelope of the stranded rope contour line
24 image data capturing device
26a-26d camera
28 data input mask
30 rope portion
32 connection line or lay line
34 connection line or wire border line
36 connection line or wire line
40 diameter correlation function
42 entropy function
44 edge detection function
45 function of the local diameter $D_m$
46 function of the brightness values along the longitudinal direction L
48 function of the local lay length $S_m$
50 adapted line
52 brightness distribution function
53 shift location
54 breakage
56 interval
58 error log
60 pictorial representation
62 rope passage opening
64 rope feed measuring device
D, $D_0$, $D_m$ diameter
$G_D$, $G_S$, $G_G$ quality value
J, $J_0$, $J_m$ longitudinal direction of wire
K, $K_0$, $K_m$ longitudinal direction of strand
L longitudinal direction
S, $S_0$, $S_m$ lay length
α lay angle
β wire angle
γ wire-strand-angle

What is claimed is:

1. A method for the computer-aided optical testing of a rope, such method implemented using at least one computer processor coupled to at least one computer storage device, the method comprising:

storing in the at least one storage device an image data set for at least one portion of the rope;

storing in the at least one storage device target values of a pictorial longitudinal extension of a representation of wires of the rope relative to a pictorial longitudinal extension of the rope in the image data set, wherein the target values electronically represent the rope as defect-free;

determining the pictorial longitudinal extension of the wires in the image data set, wherein the determining comprises adapting an estimated longitudinal extension to the image data set;

determining at least one quality value using a quality norm as a function of the determined pictorial longitudinal extension of the wires and the target values of the pictorial longitudinal extension of the wires, including comparing a wire angle of the rope with a wire angle of the rope in the image data set, wherein the wire angle is an angle that is enclosed between the longitudinal direction of the rope and the longitudinal direction of the wires;

discriminating pictorial positions within the image data set of the rope, including determining if at least one quality value exceeds or falls below a predetermined, assigned quality threshold value; and providing the discriminated pictorial positions.

2. The method according to claim 1, further comprising:

providing target values of the pictorial longitudinal extension of the representation of strands of the at least one portion of the rope relative to the pictorial longitudinal extension of the rope in the image data set;

determining the pictorial longitudinal extension of the strands in the image data set, wherein determining comprises adapting an estimated longitudinal extension to the image data set; and determining at least one lay quality value ($G_S$) by means of a lay quality norm as a function of the determined pictorial longitudinal extension of the strands and the target values of the pictorial longitudinal extension of the strands.

3. The method according to claim 2, wherein a provision of target values of the pictorial longitudinal extension of the representation of wires is performed relative to the pictorial longitudinal extension of the strands in the image data set, and wherein the determination of the pictorial longitudinal extension of the wires in the image data set is performed relative to the determined longitudinal extension of the strands.

4. The method according to claim 1, wherein the at least one determined quality value comprises a geometry quality value ($G_G$), which is determined by means of a geometry quality norm by:

as a function of a geometric distance between the determined pictorial longitudinal extension of the wires and the target values of the pictorial longitudinal extension of the wires, or as a function of a geometric distance between the determined pictorial longitudinal extensions of at least two adjacent wires.

5. The method according to claim 1, further comprising:

determining a brightness distribution function along the determined pictorial longitudinal extension of the wires, wherein the at least one determined quality value comprises a continuity quality value ($G_S$), which is determined by a continuity quality norm as a function of at least one of a brightness distribution function, a first derivative of the brightness distribution function, and a second derivative of the brightness distribution function, and/or their nth-order moments with n=0, 1, 2.

6. The method according to claim 1, further comprising:

determining the local pictorial diameter $D_m$ of the rope in the image data set;

providing target values of the local diameter $D_0$;

determining a diameter quality value ($G_D$) by means of a diameter quality norm as a function of the determined pictorial diameter $D_m$ and the target values of the local diameter $D_0$.

7. The method according to claim 1, further comprising providing target values of at least one of a spatial extension of the strands and a spatial extension of the wires, which comprises:

selecting an image data set;

determining at least two support points and a connection line defined by the support points such that the connection line substantially coincides with:

a border line between two adjacent strands, or a border line between two adjacent wires, or a center line of a strand, or a center line of one of the wires; and storing the support points on a non-transitory storage medium.

8. The method according to claim 7, wherein determining the spatial extension of the strands in the captured portion of the rope is performed by adapting an estimated longitudinal extension $K_m$ of the strands to areas of the image data set with low brightness values.

9. The method according to one claim 7, wherein determining the spatial extension of the wires in the captured portion of the rope is performed by adapting an estimated longitudinal extension $J_m$ of the wires to areas of the image data set with high brightness values.

10. The method according to claim 1, further comprising assigning the quality value to associated, discriminated, and spatial positions along the rope.

11. A computer program product comprising computer-readable instructions stored in a computer-readable memory, wherein the instructions perform a method for the computer-aided optical testing of a rope, when loaded and executed on a suitable computer system, the method comprising:

providing an image data set for at least one portion of the rope;

providing target values of a pictorial longitudinal extension of a representation of wires of the rope relative to a pictorial longitudinal extension of the rope in the image data set wherein the target values electronically represent the rope as defect-free;

determining the pictorial longitudinal extension of the wires in the image data set, wherein determining comprises adapting an estimated longitudinal extension to the image data set;

determining at least one quality value using a quality norm as a function of the determined pictorial longitudinal extension of the wires and the target values of the pictorial longitudinal extension of the wires, including comparing a wire angle of the rope with a wire angle of the rope in the image data set, wherein the wire angle is an angle that is enclosed between the longitudinal direction of the rope and the longitudinal direction of the wires;

discriminating pictorial positions within the image data set of the rope, including determining if at least one quality value exceeds or falls below a predetermined, assigned quality threshold value; and providing the discriminated pictorial positions.

12. A system for the optical testing of a rope, the system comprising:

at least one image data capturing device that optically captures at least one portion of the rope;

a target value storage unit that provides target values of at least one of a longitudinal extension $K_0$ of the strands and of a longitudinal extension $J_0$ of the wires, relative to the longitudinal extension $K_0$ of the strands, to a discriminating unit, wherein the target values electronically represent the rope as defect-free; and an image data evaluating device that determines at least one of a longitudinal extension $K_m$ of the strands in the captured portion of the rope and the longitudinal extension $J_m$ of the wires in the captured portion of the rope, relative to the determined longitudinal extension $K_m$ of the strands; and an output unit, wherein the discriminating unit:

determines one or more of:

at least one quality value using a quality norm as a function of the determined longitudinal extension $J_m$ of the wires and the target values of the longitudinal extension $J_0$ of the wires, and at least one quality value using a quality norm as a function of the determined longitudinal extension $K_m$ of the strands and the target values of the longitudinal extension $K_0$ of the strands, which includes comparing a wire angle of the rope with a wire angle of the rope in the image data set, wherein the wire angle is an angle that is enclosed between the longitudinal direction of the rope and the longitudinal direction of the wires;

discriminates the pictorial positions within the image data set of the rope, and determines if at least one quality value exceeds or falls below a predetermined, assigned quality threshold value.

13. The system according to claim 12, wherein the discriminating unit assigns the quality value to associated, discriminated, spatial positions along the rope.

14. The system according to claim 12, further comprising: a rope assessment unit that assigns an assessment feature to the pictorial or spatial positions along the rope, which are discriminated by the discriminating unit.

* * * * *